United States Patent
Miyamoto et al.

(10) Patent No.: US 9,452,236 B2
(45) Date of Patent: Sep. 27, 2016

(54) PLASMA GENERATING APPARATUS

(71) Applicant: SAMSUNG ELECTRONICS CO., LTD., Suwon-si, Gyeonggi-do (KR)

(72) Inventors: Makoto Miyamoto, Osaka (JP); Kazutoshi Takenoshita, Osaka (JP); Yukika Yamada, Osaka (JP); Yoshitaka Terao, Osaka (JP); Nobutake Hirai, Osaka (JP)

(73) Assignee: SAMSUNG ELECTRONICS CO., LTD., Suwon-Si (KR)

(*) Notice: Subject to any disclaimer, the term of this patent is extended or adjusted under 35 U.S.C. 154(b) by 122 days.

(21) Appl. No.: 14/363,481

(22) PCT Filed: Dec. 7, 2012

(86) PCT No.: PCT/JP2012/081827
§ 371 (c)(1),
(2) Date: Jun. 6, 2014

(87) PCT Pub. No.: WO2013/085045
PCT Pub. Date: Jun. 13, 2013

(65) Prior Publication Data
US 2015/0125356 A1  May 7, 2015

(30) Foreign Application Priority Data

| Dec. 8, 2011 | (JP) | 2011-268605 |
| Dec. 9, 2011 | (JP) | 2011-270445 |
| Dec. 9, 2011 | (JP) | 2011-270503 |

(51) Int. Cl.
| A61L 9/22   | (2006.01) |
| H05H 1/24   | (2006.01) |
| F24F 3/16   | (2006.01) |
| H01B 13/00  | (2006.01) |
| H01T 19/00  | (2006.01) |
| H01T 23/00  | (2006.01) |

(52) U.S. Cl.
CPC ............... *A61L 9/22* (2013.01); *F24F 3/166* (2013.01); *H01B 13/0026* (2013.01);
(Continued)

(58) Field of Classification Search
CPC ... A61L 9/22; F24F 3/166; F24F 2003/1682; H01B 13/0026; H05H 1/2406; H05H 2001/2412; H05H 2245/1225; H01T 19/00; H01T 23/00; H01J 37/32009; H01J 37/32357; H01J 37/32541; H01J 37/3244; H01J 2237/3325
See application file for complete search history.

(56) References Cited

U.S. PATENT DOCUMENTS

| 2006/0042545 A1* | 3/2006 | Shibata | ............. H01J 37/32009 118/722 |
| 2009/0211459 A1* | 8/2009 | Hu | ............................ A61L 9/22 99/357 |

FOREIGN PATENT DOCUMENTS

| JP | 2001-314751 | 11/2001 |
| JP | 2001-321633 | 11/2001 |

(Continued)

OTHER PUBLICATIONS

Extended European Search Report dated Jun. 26, 2015 in corresponding European Application No. 12855583.6.
(Continued)

Primary Examiner — Xiuyu Tai
(74) Attorney, Agent, or Firm — Staas & Halsey LLP

(57) ABSTRACT

Disclosed herein is a plasma generating apparatus capable of sufficiently performing a deodorization function and a sterilization function by increasing a generation amount of ions or radicals while suppressing generation of ozone. The plasma generating apparatus has a pair of electrodes (21 and 22) provided with dielectric films (21a and 22a) and serves to apply a predetermined voltage between the electrodes (21 and 22) to discharge plasma, fluid circulation holes (21b and 22b) are respectively provided at corresponding positions of the respective electrodes (21 and 22) and pass through the electrodes, and plasma is generated only in opening end portions (21x and 22x) forming the fluid circulation holes (21b and 22b) between the pair of electrodes (21 and 22).

17 Claims, 23 Drawing Sheets

(52) U.S. Cl.
CPC ... *H05H 1/2406* (2013.01); *F24F 2003/1682* (2013.01); *H01T 19/00* (2013.01); *H01T 23/00* (2013.01); *H05H 2001/2412* (2013.01); *H05H 2245/1225* (2013.01)

(56) References Cited

FOREIGN PATENT DOCUMENTS

| JP | 2002-273156 | 9/2002 |
| JP | 2005-123159 | 5/2005 |
| JP | 2010-149053 | 7/2010 |
| WO | WO 2008/013820 A2 | 1/2008 |
| WO | WO 2008/013820 A3 | 1/2008 |

OTHER PUBLICATIONS

Office Action mailed Dec. 17, 2015 in Chinese Patent Application No. 201280069371.4.

\* cited by examiner

INDICATES PLASMA GENERATION PREVENTION MEMBER

PLASMA GENERATING APPARATUS

CROSS REFERRENCE TO RELATED APPLICATIONS

This application is the U.S. National Stage of International Application No. PCT/JP2012/081827, filed Dec. 7, 2012, and claims priority to Japanese Application No. 2011-268605, filed Dec. 8, 2011, Japanese Application No. 2011-270503, filed Dec. 9, 2011, and Japanese Application No. JP2011-270445, filed Dec. 9, 2011, the disclosures of which are incorporated herein in their entirety by reference.

TECHNICAL FIELD

The present invention relates to a plasma generating apparatus and a plasma generating method.

BACKGROUND ART

Recently, there is an increasing need for air quality control such as sterilization and deodorization in a living environment, due to an increase in carriers of atopy, asthma, and allergic symptoms, and increased risk of infection such as seen in the explosive prevalence of new influenza. In addition, as living standards improve, an amount of food storage and a chance of storing leftover food are increased. Accordingly, the importance of environmental control in storage equipment such as a refrigerator is also growing.

In the related art intended to control air quality of a living environment, physical control as represented by a filter is generally used. According to physical control, relatively large dust and debris floating in the air may be captured, and bacteria, viruses, or the like may also be captured depending on the size of a filter hole. In addition, in a case that there are an immense number of adsorption sites such as in activated carbon, it may be possible to capture odor-causing molecules. However, there are problems in that air in a space to be controlled is required to evenly pass through the filter in order to capture these substances, the apparatus is increased in size, and maintenance costs such as filter replacement are also increased while having no effect on adhesive substances. Therefore, as a means to enable sterilization and deodorization of adhesive substances, it may be exemplified to release chemically active species in a space to be sterilized and deodorized. In spraying of chemicals or release of flavoring agents or deodorants, it is necessary to prepare the active species in advance and regular replenishment thereof is essential. On the other hand, a means to perform sterilization and deodorization using the chemically active species created by generating plasma in the atmosphere is increased in recent years.

Technologies to perform sterilization and deodorization by ions or radicals generated by discharge of plasma into the atmosphere may be classified into the following two types:

(1) a so-called passive type plasma generating apparatus in which bacteria and viruses floating in the atmosphere (hereinafter, referred to as "floating bacteria") or malodorous substances (hereinafter, referred to as "odors") react with ions or radicals within a limited capacity in the apparatus (for example, see Patent Document 1); and (2) a so-called active type plasma generating apparatus in which ions or radicals generated by a plasma generating portion are released into a closed space (e.g., a living room, a toilet, a car interior, or the like) having a larger capacity than (1), and the ions or radicals react with floating bacteria or odors by a collision therewith in the atmosphere (for example, see Patent Document 2).

The passive type plasma generating apparatus of (1) has an advantage that high sterilization and deodorization effects may be expected because ions or radicals having high concentrations are created by generation of plasma in the small capacity. Meanwhile, the apparatus has a disadvantage that the size thereof is increased because floating bacteria or odors must be introduced into the apparatus, ozone as a common by-product of plasma generation is likely to occur, and a filter for adsorption or decomposition must be separately installed in order to prevent ozone from leaking out of the apparatus.

Next, the active type plasma generating apparatus of (2) has an advantage that the apparatus may be relatively small, and sterilization of bacteria (hereinafter, referred to as "adhesive bacteria") adhered to a surface of clothing or decomposition of odors adsorbed onto the surface may be expected in addition to sterilization of floating bacteria or decomposition of odors in the air. Meanwhile, the apparatus has a disadvantage that only long-lived active species cannot help but expect sterilization and deodorization effects because ions or radicals are diffused within the closed space, which is very large compared to the volume of the apparatus, and have low concentrations. As a result, the deodorization effect may not be nearly effective in a space having a high odor concentration (a high concentration of 10,000 times that of active species).

From the above, in the passive type plasma generating apparatus, the effect is limited only to floating bacteria or odors contained in an air stream flowing into the apparatus. On the other hand, in the active type plasma generating apparatus, such effect cannot help but be expected only with respect to floating bacteria, adhesive bacteria, and odors having low concentrations. In other words, only either "sterilization and deodorization of floating bacteria" or "sterilization of floating bacteria and adhesive bacteria having low concentrations and deodorization of adhesive odors" may be realized using the related art.

However, there are some situations where sterilization of adhesive bacteria having high concentrations and deodorization of odors having high concentrations are required to be simultaneously performed in a daily life environment. The most typical example is a refrigerating chamber of a refrigerator in which many bacteria adhered to surfaces of food and a storage container surfaces exist and odors arising from food itself and decayed leftover food also exist.

CITATION LIST

Patent Document

Patent Document 1: Japanese Unexamined Patent Application Publication No. 2002-224211
Patent Document 2: Japanese Unexamined Patent Application Publication No. 2003-79714

DISCLOSURE

Technical Problem

From the above, the present inventors contemplate an increase in a generation amount of ions or radicals so as to simultaneously include both a passive function which deodorizes adhesive bacteria using ions or radicals by generation of plasma and an active function which sterilizes the adhesive bacteria by release of the ions or radicals. To this end, the present inventors execute an improvement in a plasma generating apparatus which has a pair of electrodes provided with a dielectric film on at least one side of facing surfaces thereof and serves to apply a predetermined voltage between the electrodes to discharge plasma, wherein fluid circulation holes are respectively provided at corresponding positions of the respective electrodes and pass through the electrodes.

The present inventors examine the material, structure, or thickness of the dielectric film provided on the electrode, the voltage value or pulse width of a pulse voltage as a predetermined voltage, or the like, in order to suppress generation of ozone and simultaneously realize high concentrations of ions or radicals in the plasma generating apparatus. As a result of further examining the plasma generating apparatus, the present inventors have found that ions or radicals are superiorly generated at an opening end portion of the fluid circulation hole on each electrode and ozone is superiorly generated at a portion except for the opening end portion on each electrode.

Therefore, it is an object of the present invention to sufficiently perform a function which deodorizes floating bacteria and adhesive bacteria by ions or radicals and a function which sterilizes the floating bacteria and adhesive bacteria by release of the ions or radicals to the outside of the apparatus, by increasing a generation amount of ions or radicals while suppressing generation of ozone.

Technical Solution

In accordance with an aspect of the present invention, a plasma generating apparatus has a pair of electrodes provided with a dielectric film on at least one side of facing surfaces thereof and serves to apply a predetermined voltage between the electrodes to discharge plasma, wherein fluid circulation holes are respectively provided at corresponding positions of the respective electrodes and pass through the electrodes and plasma is generated only in opening end portions forming the fluid circulation holes between the pair of electrodes.

In addition, the corresponding positions mean that the fluid circulation holes formed in the pair of electrodes are substantially in the same positions and face each other when viewed from a face plate direction of each electrode. In addition, the corresponding positions mean the same substantially coordinate position (x, y) at both electrodes when viewing the pair of electrodes on the x-y plane from the z-axis direction in the orthogonal coordinate system.

Accordingly, since plasma is generated only in the opening end portions forming the fluid circulation holes between the pair of electrodes, ions or radicals may be superiorly generated by generating plasma only in the opening end portions and plasma is not generated in the portions except for the opening end portions in which ozone is superiorly generated. Consequently, it may be possible to sufficiently perform a function which deodorizes floating bacteria and adhesive bacteria by ions or radicals and a function which sterilizes the floating bacteria and adhesive bacteria by release of the ions or radicals to the outside of the apparatus, by increasing a generation amount of ions or radicals while suppressing generation of ozone. In addition, since the dielectric film are provided in at least one side of the pair of electrodes, a spacer to define a gap for plasma formation between the respective electrodes is not required and the gap may be formed between the facing surfaces.

As an aspect which is specifically realized such that plasma is generated only in the opening end portions of the fluid circulation holes, a facing distance between the opening end portions forming the fluid circulation holes may be smaller than a facing distance between portions except for the opening end portions, and when a predetermined voltage is applied between the pair of electrodes, plasma may be discharged only in the opening end portions forming the fluid circulation holes. Consequently, plasma may be generated only in the opening end portions of the fluid circulation holes only by adjusting the facing distance between the opening end portions forming the fluid circulation holes and the facing distance between portions except for the opening end portions.

In order for facing distance between the opening end portions forming the fluid circulation holes to be smaller than the facing distance between portions except for the opening end portions, a thickness of the dielectric film formed at each of the opening end portions forming the fluid circulation holes may be thicker than a thickness of the dielectric film formed at the portion except for the opening end portions. Consequently, plasma may be generated only in the opening end portions of the fluid circulation holes only by adjusting the thickness of the dielectric film.

In order to generate plasma throughout an opening circumference of each of the fluid circulation holes, a thickness of the dielectric film formed on overall circumference of each of the opening end portions may be thicker than a thickness of the dielectric film formed at the portion except for the opening end portions.

Specifically, a difference between the thickness of the dielectric film formed at each of the opening end portions and the thickness of the dielectric film formed at the portion except for the opening end portions may be 1 µm to 500 µm.

In addition, a plasma generation prevention member to prevent generation of plasma may be provided in a portion except for the opening end portions forming the fluid circulation holes of the respective electrodes. In addition, the corresponding positions mean that the fluid circulation holes formed in the pair of electrodes are substantially in the same positions and face each other when viewed from a face plate direction of each electrode. In addition, the corresponding positions mean the same substantially coordinate position (x, y) at both electrodes when viewing the pair of electrodes on the x-y plane from the z-axis direction in the orthogonal coordinate system.

In accordance with such a plasma generating apparatus, since the plasma generation prevention members are provided in the portions except for the opening end portions forming the fluid circulation holes, it may be possible to generate plasma in the opening end portions and to reduce plasma generated in the portions except for the opening end portions. Ions or radicals are superiorly generated in the plasma of the opening end portions and ozone is superiorly generated in the plasma of the portions except for the opening end portions. Therefore, it may be possible to sufficiently perform a function which deodorizes floating bacteria and adhesive bacteria by ions or radicals and a function which sterilizes the floating bacteria and adhesive bacteria by release of the ions or radicals to the outside of the apparatus, by increasing a generation amount of ions or radicals while suppressing generation of ozone. In addition, since the dielectric film are provided in at least one side of the pair of electrodes, a spacer to define a gap for plasma formation between the respective electrodes is not required and the gap may be formed between the facing surfaces.

When the plasma generation prevention member is too spaced apart from the opening end of the fluid circulation hole, ozone is superiorly generated. Therefore, the plasma generation prevention member may be preferably provided beyond a range of 0 μm to 500 μm from an opening end forming each of the fluid circulation holes.

In order to suppress generation of ozone such that plasma is generated only in the opening end portions while being not generated in the portions except for the opening end portions, the plasma generation prevention member may be provided in an overall portion except for the opening end portions between the pair of electrodes.

In order to secure insulation between the pair of electrodes, the plasma generation prevention member may be made of a low dielectric material having a relative dielectric constant of 30 or less.

When a gap is present between the plasma generation prevention member and the facing surface of each electrode or the dielectric film, plasma may be generated in the gap. Therefore, the plasma generation prevention member may be preferably pressed against the facing surface of each electrode or the dielectric film.

In order to simplify the configuration of the plasma generating apparatus without a separate fixing member to fix the pair of electrodes in a state of facing each other, the pair of electrodes may adhere to each other by the plasma generation prevention member.

In order to simplify fixing of the plasma generation prevention member, the plasma generation prevention member may be interposed and fixed between the pair of electrodes. In addition, in this case, a fixing member to fix the pair of electrodes in a state of facing each other is required.

In order to enhance generation of ions or radicals and increase a deodorization effect by allowing fluid to pass through the fluid circulation holes, a blower mechanism may be provided upstream or downstream of the fluid circulation holes and wind is blown into the fluid circulation holes by the blower mechanism. Here, the blower mechanism may allow a flow rate of the wind passing through the fluid circulation holes to be within a range of 0.1 m/s to 10 m/s.

The thickness of the dielectric film may be easily controlled by forming the dielectric film using sputtering.

In order to increase a generation amount of active species such as ions or radicals while suppressing a generation amount of ozone in the opening end portions forming the fluid circulation holes, the voltage applied to each electrode may be formed in a pulse shape, a peak value thereof may be set within a range of 100 V to 5000 V, and a pulse width may be set within a range of 0.1 μs to 300 μs.

In accordance with another aspect of the present invention to simultaneously realize both sterilization and deodorization of adhesive bacteria, a plasma generating apparatus has a pair of electrodes provided with a dielectric film on at least one side of facing surfaces thereof and serves to apply a predetermined voltage between the electrodes to discharge plasma, wherein fluid circulation holes being respectively provided at corresponding positions of the respective electrodes and passing through the electrodes while a through hole is provided separately from the fluid circulation holes in the electrode of one side and the through hole is blocked, at an opening of a facing surface side thereof, by the electrode of the other side, and a thickness of the dielectric film formed at each of the opening end portions forming the fluid circulation holes and a thickness of the dielectric film formed at the opening end portion forming the through hole are thicker than a thickness of the dielectric film formed at the portion except for the opening end portions.

Accordingly, fluid passing through the fluid circulation holes may further come into contact with plasma via the through hole or fluid before passing through the fluid circulation holes may previously come into contact with plasma via the through hole. Therefore, it may be possible to increase a generation amount of ions or radicals. In this case, since the thickness of the dielectric film formed at each of the opening end portions forming the fluid circulation holes and the thickness of the dielectric film formed at the opening end portion forming the through hole are thicker than the thickness of the dielectric film formed at the portion except for the opening end portions, ions or radicals may be superiorly generated by generating plasma only in the opening end portions and plasma is not generated in the portions except for the opening end portions in which ozone is superiorly generated. Consequently, it may be possible to sufficiently perform a function which deodorizes floating bacteria and adhesive bacteria by ions or radicals and a function which sterilizes the floating bacteria and adhesive bacteria by release of the ions or radicals to the outside of the apparatus, by increasing a generation amount of ions or radicals while suppressing generation of ozone.

In accordance with another aspect of the present invention to simultaneously realize both sterilization and deodorization of adhesive bacteria, a plasma generating apparatus has a pair of electrodes provided with a dielectric film on at least one side of facing surfaces thereof and serves to apply a predetermined voltage between the electrodes to discharge plasma, wherein fluid circulation holes are respectively provided at corresponding positions of the respective electrodes and pass through the electrodes while a through hole is provided separately from the fluid circulation holes in the electrode of one side and the through hole is blocked, at an opening of a facing surface side thereof, by the electrode of the other side, and a plasma generation prevention member is provided in a portion except for opening end portions forming the fluid circulation holes between the pair of electrodes, an opening end portion forming the through hole, and a portion facing the same.

Accordingly, fluid passing through the fluid circulation holes may further come into contact with plasma via the through hole or fluid before passing through the fluid circulation holes may previously come into contact with plasma via the through hole. Therefore, it may be possible to increase a generation amount of ions or radicals. In this case, since the plasma generation prevention member is provided in a portion except for opening end portions forming the fluid circulation holes between the pair of electrodes, an opening end portion forming the through hole, and a portion facing the same, ions or radicals may be superiorly generated by generating plasma only in the opening end portions and plasma is not generated in the portions except for the opening end portions in which ozone is superiorly generated. Consequently, it may be possible to sufficiently perform a function which deodorizes floating bacteria and adhesive bacteria by ions or radicals and a function which sterilizes the floating bacteria and adhesive bacteria by release of the ions or radicals to the outside of the apparatus, by increasing a generation amount of ions or radicals while suppressing generation of ozone.

In accordance with another aspect of the present invention to simultaneously realize both sterilization and deodorization of adhesive bacteria, a plasma generating apparatus has a pair of electrodes facing each other and serves to apply a predetermined voltage between the electrodes to discharge plasma, wherein the respective electrodes have insulation substrates, conductive films formed on facing surfaces of the insulation substrates, and dielectric films formed on the conductive films, respectively, while fluid circulation holes are respectively provided at corresponding positions of the respective electrodes and pass through the electrodes, and each of the conductive films is selectively formed in a predetermined region in which plasma is discharged among the facing surfaces of the insulation substrates.

Accordingly, since a plasma discharge region is specified using the insulation substrate such as a ceramic substrate and the conductive film is selectively formed in the region, instead of the conductive substrate made of metal used in the related art, it may be possible to select chemical species generated by plasma discharge and to superiorly generate active species such as ions or radicals or superiorly generate ozone. Therefore, in accordance with the present invention, it may be possible to control generation of active species such as ions or radicals and generation of ozone by changing a region formed with the conductive film according to the use thereof and to improve sterilization and deodorization effects while securing safety.

Specifically, when active species such as ions or radicals are intended to be superiorly generated, each of the conductive films may be formed in a region (A) within 1 mm from an opening circumference of the associated fluid circulation hole among the facing surfaces of the insulation substrates.

Meanwhile, when ozone is intended to be superiorly generated, each of the conductive films may be formed in a region (B) spaced over 1 mm from an opening circumference of the associated fluid circulation hole among the facing surfaces of the insulation substrates.

In a case where the conductive films are formed in a region (A) within 1 mm from an opening circumference of the associated fluid circulation hole and in a region (B) spaced over 1 mm from an opening circumference of the associated fluid circulation hole, among the facing surfaces of the insulation substrates, and the conductive film formed in the region (A) is electrically isolated from the conductive film formed in the region (B), it may be possible to change what to superiorly generate any one of active species such as ions or radicals and ozone by selecting what to apply current to any one of the conductive films.

The present inventors examine a change in ion number and ozone concentration by changing a ratio between the region (A) and the region (B) using three types of electrodes having through holes which are differently arranged from each other and by discharging plasma under the following conditions.

Applied voltage: 700 V
Pulse width: 5 μs
Frequency: 1 kHz
Air blowing: installation of a fan such that the flow rate of the wind passing through the through hole of the electrode is 2 m/s
Ion number measurement: measurement of the ion number by an air ion measuring instrument at the distance of 100 mm from the electrode
Ozone concentration measurement: measurement of the ozone concentration by installing a sampling tube of an ozone concentration system at the distance of 10 mm from the electrode As a result, as shown in FIGS. 22 and 23, it is observed that, even when the applied voltage, the pulse width, and the frequency are changed, the ion number is increased and the ozone concentration is decreased as the ratio of the region (A) is increased (that is, as the ratio of the region (A) is decreased).

In order to accurately control what to superiorly generate any one of active species such as ions or plasma and ozone, the dielectric films may be formed only on the conductive films and in the vicinity thereof.

In order to form a gap between the electrodes to generate plasma without using a spacer, each of the dielectric films may have surface roughness (Rz) of 1 to 100 μm.

Each of the dielectric films may be made of a material containing at least one compound selected from a group consisting of $CaO$, $Al_2O_3$, $SiO_2$, $B_2O_3$, $ZrO_2$, and $TiO_2$.

Each of the dielectric films may be made of a material containing at least one element selected from a group consisting of Ba, Ti, Ca, Zr, Sr, Y, and Mg as a constituent element thereof Furthermore, such a material may include at least one compound selected from a group consisting of an oxide, a carbide, a nitride, and a boride.

Each of the dielectric films may be made of a material containing at least one element selected from a group consisting of Ag, Au, Cu, Ni, Pt, Pd, Ru, and Ir as a constituent element thereof.

A means to form the dielectric film may include, for example, green sheet, screen printing, gravure printing, inkjet, dispenser, physical vapor deposition, or the like.

A means to form the insulation substrate may include, for example, green sheet, press forming, and the like.

A means to form the conductive film may include, for example, screen printing, gravure printing, inkjet, dispenser, physical vapor deposition, and the like.

In accordance with a further aspect of the present invention, a method of manufacturing a plasma generating apparatus is also one present invention. The method includes applying conductive pastes on the insulation substrates to form a predetermined conductive pattern, overlapping materials to form the dielectric films on the conductive patterns, and forming the electrodes by simultaneously heating and firing the insulation substrates, the conductive patterns, and the materials to form the dielectric films.

Accordingly, since the electrode may be easily manufactured by a minimal process compared to the related art, it may be possible to reduce manufacturing costs. In addition, according to the present invention, since the electrode may be manufactured in various shapes or structures, it may be possible to obtain the degree of freedom of design with respect to the electrode according to use thereof.

Advantageous Effects

In accordance with the present invention having such a configuration, it may be possible to sufficiently perform a function which deodorizes floating bacteria and adhesive bacteria by ions or radicals and a function which sterilizes the floating bacteria and adhesive bacteria by release of the ions or radicals to the outside of the apparatus, by increasing a generation amount of ions or radicals while suppressing generation of ozone.

DESCRIPTION OF DRAWINGS

The above and other objects, features and other advantages of the present invention will be more clearly understood from the following detailed description taken in conjunction with the accompanying drawings, in which.

REFERENCE SIGNS LIST

Figure 1:
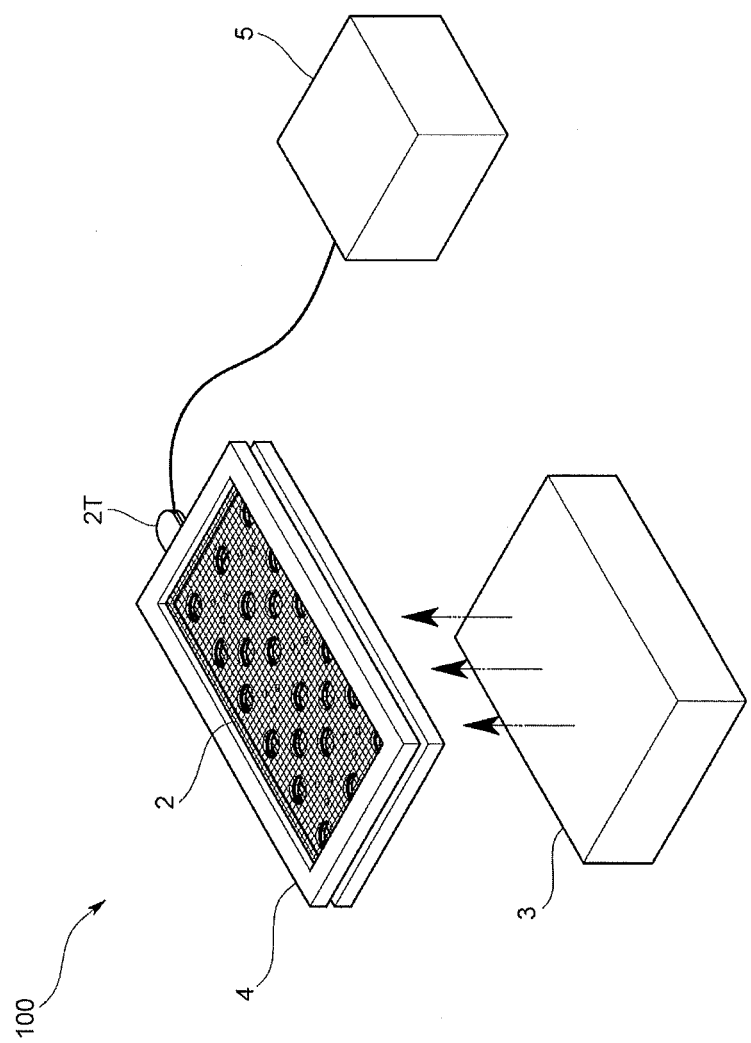
FIG. 1 is a perspective view illustrating a plasma generating apparatus according to a first embodiment of the present invention.

100: plasma generating apparatus
21: electrode of one side
22: electrode of the other side
21a, 22a: dielectric film
21b, 22b: fluid circulation hole
21x, 22x: opening end portion forming fluid circulation hole
21c: through hole
21y: opening end portion forming through hole
L1: facing distance between opening end portions forming fluid circulation holes
L3: facing distance between portions except for opening end portion
t1: thickness of dielectric film of opening end portion
t3: thickness of dielectric film of portion except for opening end portion
3: blower mechanism
6: plasma generation prevention member
21f, 22f: ceramic substrate
21g, 22g: conductive film Best Mode

[1. First Embodiment]

Hereinafter, an embodiment of the present invention will be described with reference to the drawings.

A plasma generating apparatus 100 according to the present invention is used for a household appliance such as a refrigerator, a washing machine, a cleaner, a clothing dryer, an air conditioner, or an air cleaner, and serves to deodorize air in the inside or outside of the household appliance and to sterilize floating bacteria or adhesive bacteria in the inside or outside of the household appliance.

Figure 2:
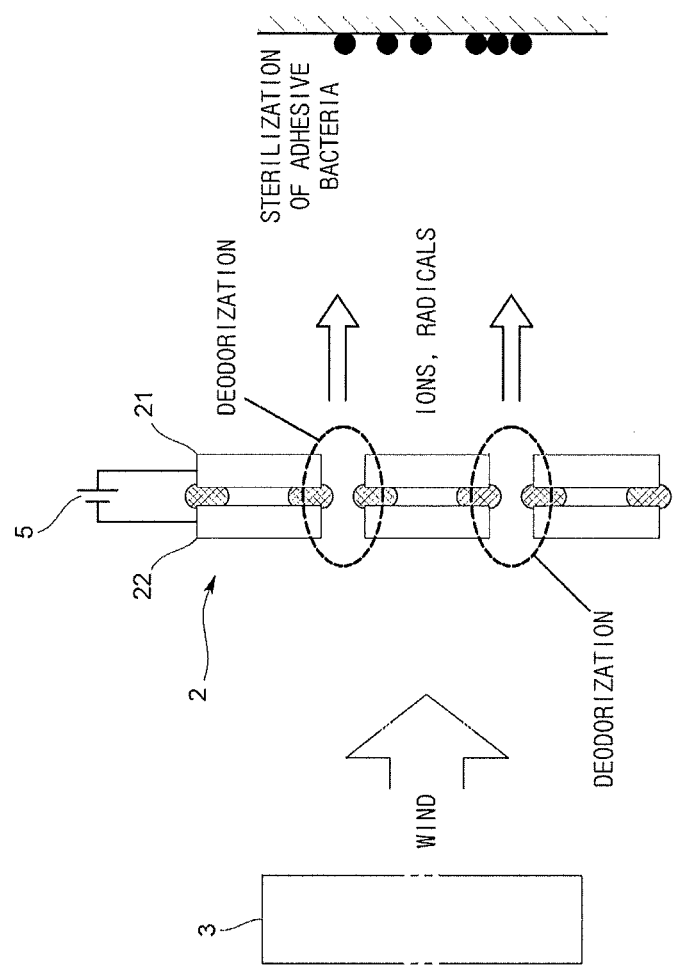
FIG. 2 is a diagram illustrating operation of the plasma generating apparatus according to the first embodiment.

Specifically, as shown in FIGS. 1 and 2, the plasma generating apparatus 100 includes a plasma electrode portion 2 to generate ions or radicals using Micro Gap Plasma, a blower mechanism 3 which is provided outside the plasma electrode portion 2 to forcibly blow wind (an air stream) toward the plasma electrode portion 2, an explosion-proof mechanism 4 which is provided outside the plasma electrode portion 2 so that flame generated by the plasma electrode portion 2 is not spread to the outside, and a power source 5 to apply a high voltage to the electrode portion 2.

Hereinafter, the respective portions 2 to 5 will be described with reference to the drawings.

Figure 3:
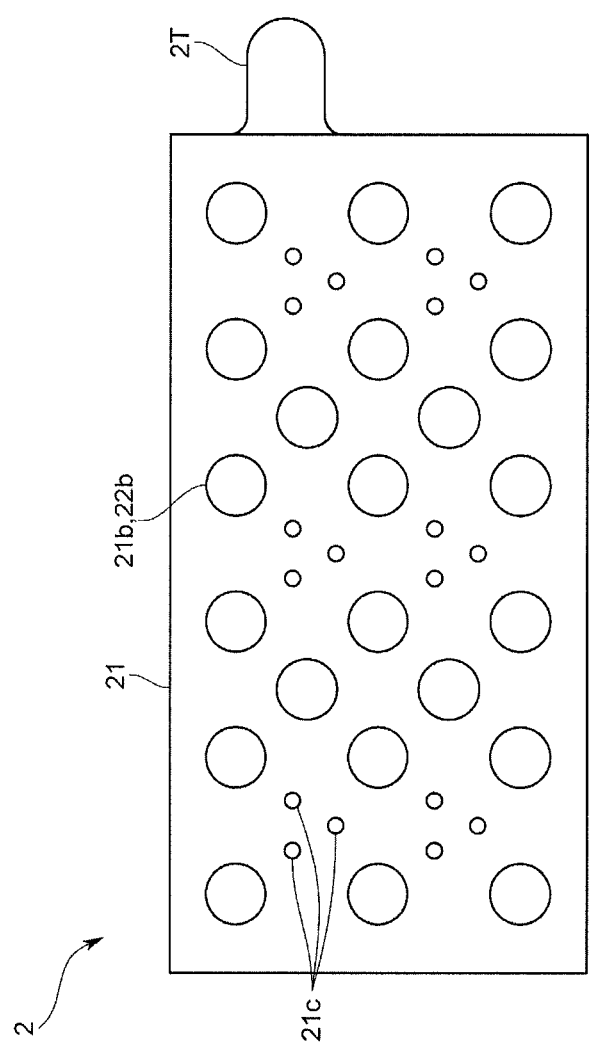
FIG. 3 is a top view illustrating an electrode portion according to the first embodiment.

As shown in FIGS. 2 to 6, the plasma electrode portion 2 has a pair of electrodes 21 and 22 provided with dielectric films 21a and 22a on respective facing surfaces thereof, and serves to apply a predetermined voltage between the electrodes 21 and 22 and discharge plasma. In particular, as shown in FIG. 3, each of the electrodes 21 and 22 has a substantially rectangular shape in the plan view (when viewed from a face plate direction of the electrode 21 or 22), and is made of stainless steel such as SUS403, for example. An edge portion of the electrode 21 or 22 of the electrode portion 2 is formed with an applied terminal 2T to which a voltage is applied from the power source 5 (see FIG. 3).

Figure 10:
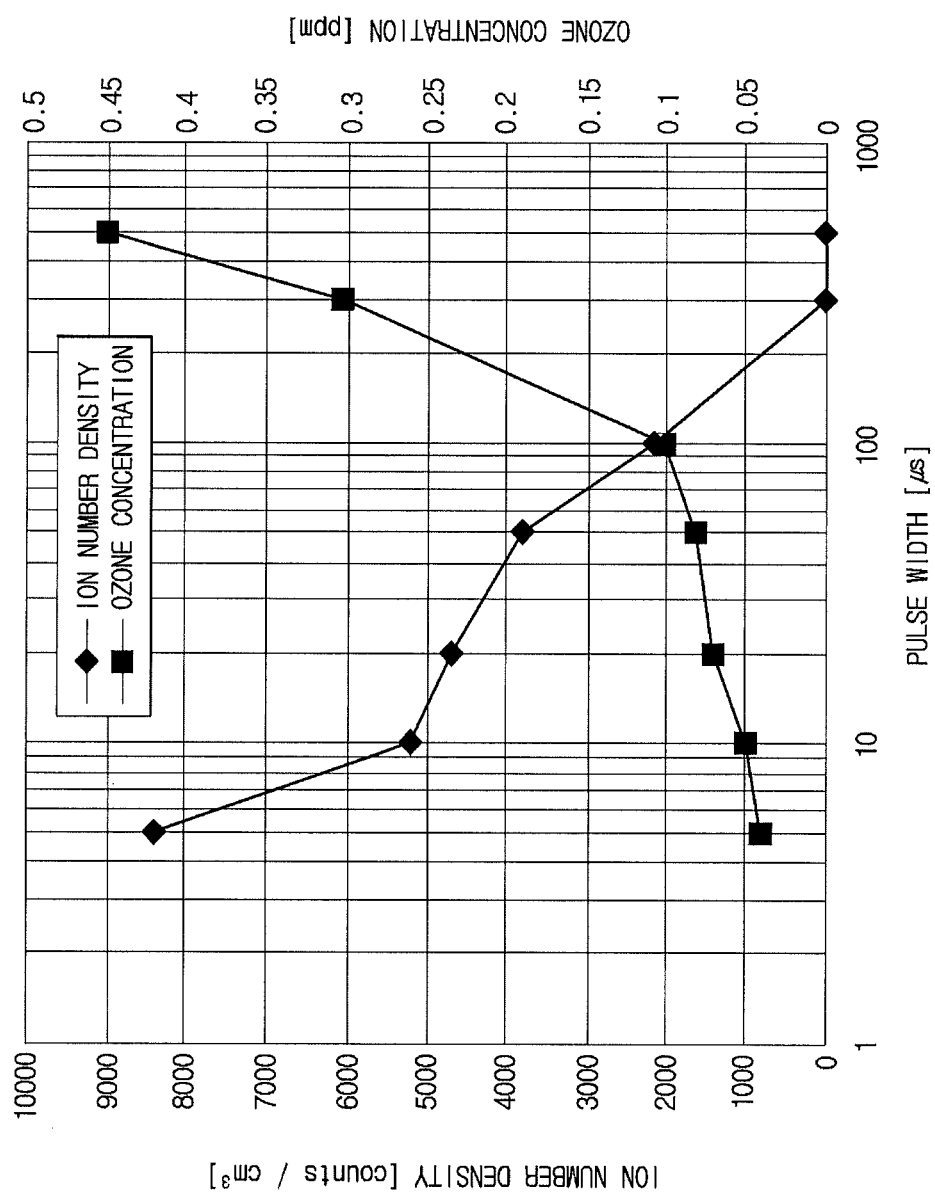
FIG. 10 is a graph illustrating pulse width dependence of an ion number density and an ozone concentration according to the first embodiment.

Here, a method of applying the voltage to plasma electrode portion 2 by the power source 5 is made by forming the voltage applied to each electrode 21 or 22 in a pulse shape, setting a peak value thereof within a range of 100 V to 5000 V, and setting a pulse width within a range of 0.1 µs to 300 ms. As shown in FIG. 10, an ion number density is measured and an ozone concentration is lowered in a case in which the pulse width is equal to or less than 300 µs. As the pulse width is small, the ion number is increased and the ozone concentration is decreased.

Consequently, it may be possible to suppress a generation amount of ozone and to effectively release active species generated by plasma without loss of a filter occurring in the related art. As a result, it may be possible to sterilize adhesive bacteria in a short time.

Figure 5:
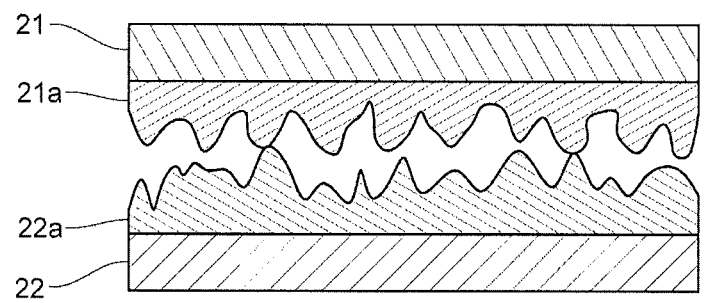
FIG. 5 is an enlarged cross-sectional view illustrating a configuration of a facing surface of the electrode portion according to the first embodiment.

In addition, as shown in FIG. 5, the respective facing surfaces of the electrodes 21 and 22 are formed with the dielectric films 21a and 22a by application of dielectric such as barium titanate, for example. The dielectric films 21a and 22a have surface roughness (calculation mean roughness Ra in the embodiment) of 0.1 μm to 100 μm. These other surface roughness may also be defined using a maximum height Ry and ten point mean roughness Rz. A gap is defined between the facing surfaces by adjusting plane roughness of the dielectric films 21a and 22a to a value within the above range and just overlapping the respective electrodes 21 and 22, so that plasma is generated within the gap. In addition, the surface roughness of the dielectric films 21a and 22a is considered to be controlled by a thin film forming method such as sputtering. In addition, aluminum oxide, titanium oxide, magnesium oxide, strontium titanate, silicon oxide, silver phosphate, lead zirconate titanate, silicon carbide, indium oxide, cadmium oxide, bismuth oxide, zinc oxide, iron oxide, carbon nanotube, or the like may also be used as the dielectric applied to the electrodes.

Figure 4:
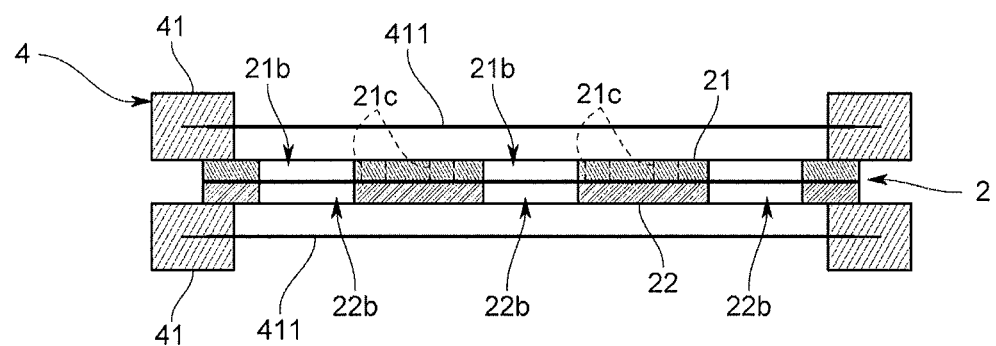
FIG. 4 is a cross-sectional view illustrating an electrode portion and an explosion-proof mechanism according to the first embodiment.
Figure 6:
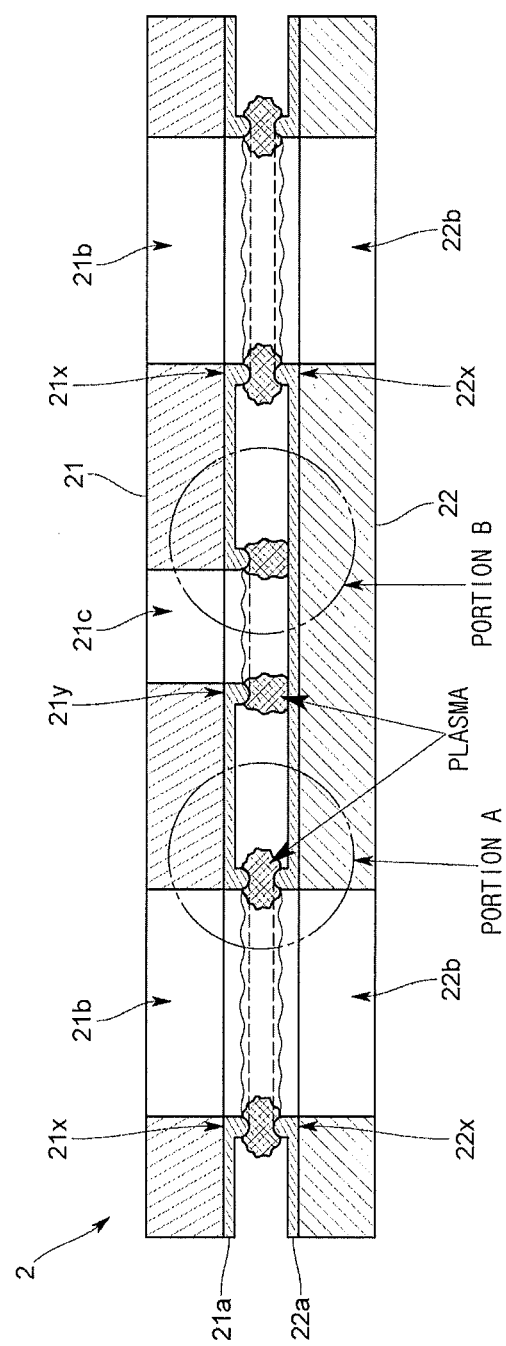
FIG. 6 is a partial enlarged cross-sectional view schematically illustrating a fluid circulation hole and a through hole according to the first embodiment.

Furthermore, as shown in FIGS. 3, 4, and 6, the electrodes 21 and 22 are respectively provided with fluid circulation holes 21b and 22b at corresponding positions of the respective electrodes 21 and 22 such that the respective electrodes 21 and 22 are configured to be penetrated by communication of the fluid circulation holes 21b and 22b. In the embodiment, as shown in FIG. 3, each of the fluid circulation hole 22b has a substantially rectangular shape when viewed from the face plate direction of the electrode 21 or 22 (in the plan view), and outlines of the respective corresponding fluid circulation holes 21b and 22b of the electrodes 21 and 22 are configured so as to coincide with each other.

In addition, when viewed from the face plate direction of the electrode 21 or 22 (in the plan view), at least a portion of the outlines of the respective corresponding fluid circulation holes 21b and 22b may also be configured so as to be arranged at positions different from each other. Specifically, an opening size (opening diameter) of the fluid circulation hole 21b formed in the electrode 21 of one side is smaller (for example, the opening diameter is small by 10 μm or more) than an opening size (opening diameter) of the fluid circulation hole 22b formed in the electrode 22 of the other side.

In addition, the plasma electrode portion 2 in the present embodiment, as shown in FIGS. 3 and 6, is configured so that a through hole 21c is provided separately from the fluid circulation holes 21b and 22b in the electrode 21 of one side and the through hole 21c is blocked, at an opening of the facing surface side thereof, by the electrode 22 of the other side.

The blower mechanism 3 is disposed on the side of the other electrode 22 of the plasma electrode portion 2, and has a blowing fan which forcibly sends wind toward the fluid circulation holes (full opening portions) 21b and 22b formed in the plasma electrode portion 2. Specifically, the blower mechanism 3 allows a flow rate of the wind passing through the fluid circulation holes 21b and 22b to be within a range of 0.1 m/s to 30 m/s.

As shown in FIG. 4, the explosion-proof mechanism 4 has protective covers 41 disposed outside the pair of electrodes 21 and 22, and is configured so that flame generated by plasma by introduction of inflammable gas into the fluid circulation holes 21b and 22b is not spread beyond the protective covers 41 to the outside. Specifically, the explosion-proof mechanism 4 has metal meshes 411 in which the protective covers 41 are disposed at the outer sides of the pair of electrodes 21 and 22. The wire diameter of each metal mesh 411 is within a range of 1.5 mm or less, and the opening ratio of the metal mesh 411 is 30% or more.

However, the plasma generating apparatus 100 in the present embodiment is configured such that plasma is generated only in opening end portions 21x and 22x forming the fluid circulation holes 21b and 22b between the pair of electrodes 21 and 22, an opening end portion 21y forming the through hole 21c, and a portion facing the same. In addition, the opening end portions 21x, 22x, and 21y are regions in which ozone is inferiorly generated compared to ions or radicals, and the regions are, for example, in a range of about a few 10 μm to about 1 mm from an opening end.

Figure 7:
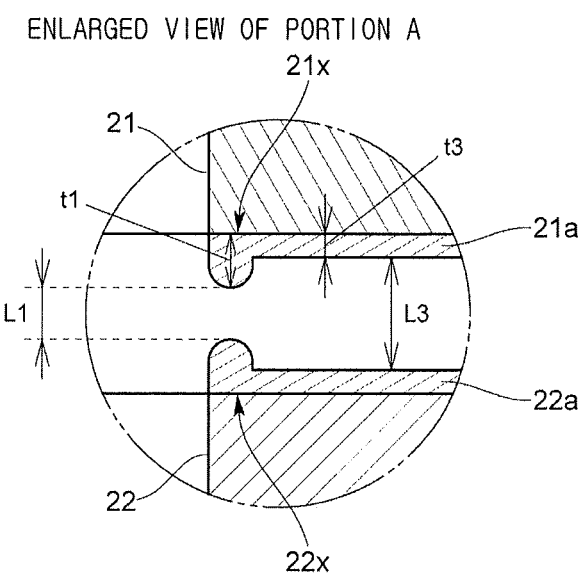
FIG. 7 is an enlarged cross-sectional view schematically illustrating an opening end portion forming the fluid circulation hole according to the first embodiment.

Specifically, as shown in FIGS. 6 and 7, in the pair of electrodes 21 and 22, a facing distance L1 between the opening end portions 21x and 22x forming the fluid circulation holes 21b and 22b facing each other and a facing distance L2 between the opening end portion 21y forming the through hole 21c and the dielectric film 22a facing the same are smaller than a facing distance L3 between portions except for the opening end portions. When the above-mentioned pulse voltage is applied between the pair of electrodes 21 and 22, plasma is generated only in the opening end portions 21x and 22x forming the fluid circulation holes 21b and 22b facing each other, the opening end portion 21y forming the through hole 21c, and the dielectric film 22a facing the same.

Figure 8:
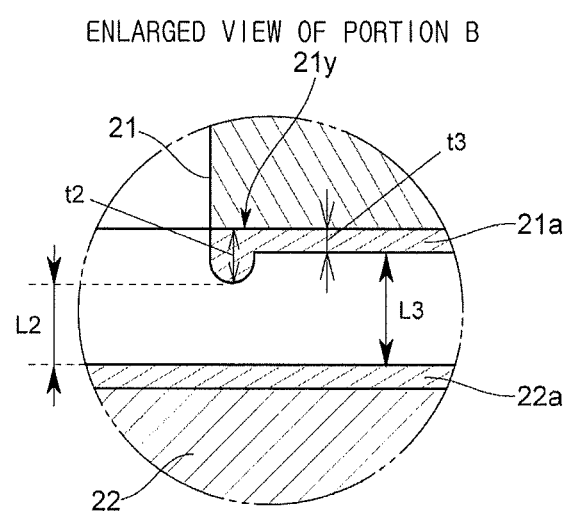
FIG. 8 is a perspective view schematically illustrating the opening end portion forming the fluid circulation hole according to the first embodiment.
Figure 9:
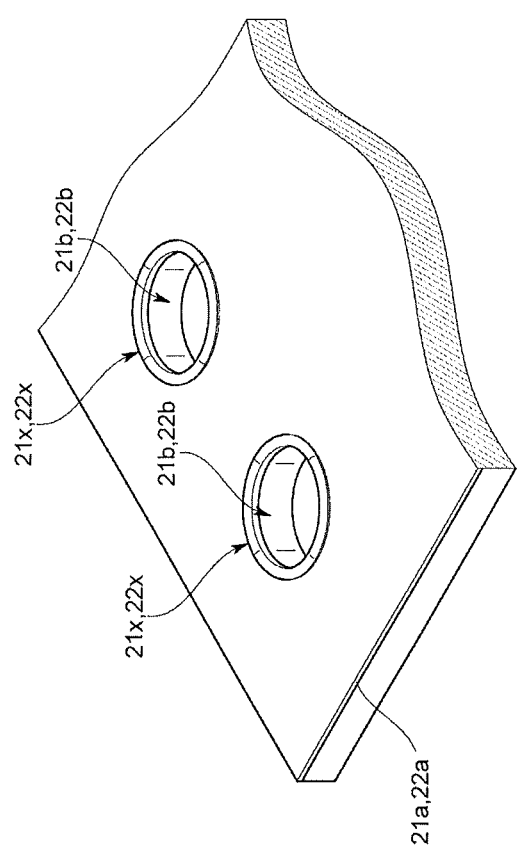
FIG. 9 is an enlarged cross-sectional view schematically illustrating an opening end portion forming the through hole according to the first embodiment.

In more detail, as shown in FIGS. 7 and 8, a thickness t1 of each of the dielectric films 21a and 22a at the opening end portions 21x and 22x forming the fluid circulation holes 21b and 22b on the facing surfaces and a thickness t2 of the dielectric film 21a at the opening end portion 21y forming the through hole 21c on the facing surface are thicker than a thickness t3 of each of the dielectric films 21a and 22a at the portions except for the opening end portions on the facing surfaces. Here, a difference between the thickness t1 of each of the dielectric films 21a and 22a at the opening end portions 21x and 22x and the thickness t3 of each of the dielectric films 21a and 22a at the portions except for the opening end portions is 10 μm to 500 μm. In addition, a difference between thickness t2 of the dielectric film 21a at the opening end portion 21y forming the through hole 21c on the facing surface and the thickness t3 of each of the dielectric films 21a and 22a at the portions except for the opening end portions is also 10 μm to 500 μm. In addition, the difference between the thicknesses of the films means a thickness of the mean film considering the surface roughness. In the embodiment, as shown in FIG. 9, the thicknesses t1 and t2 of the dielectric films 21a and 22a are thicker than the thickness t3 of each of the dielectric films 21a and 22a at the portions except for the opening end portions while being formed in an annular shape throughout circumferences of the opening end portions 21x and 22x forming the fluid circulation holes 21b and 22b and the opening end portion 21y forming the through hole 21c.

In the embodiment, by overlapping the pair of electrodes 21 and 22 having such a configuration such that the dielectric films 21a and 22a face each other, the dielectric film 21a at the opening end portion 21x forming the fluid circulation hole 21b comes into contact with the dielectric film 22a at the opening end portion 22x forming the fluid circulation hole 22b. In this case, a gap is formed between the dielectric films 21a and 22a by irregularity due to the surface roughness of the dielectric films 21a and 22a so that plasma is generated within the gap. In addition, FIGS. 6 and 7 show that the dielectric films 21a and 22a are spaced apart from each other for convenience. Meanwhile, since the facing distance between the dielectric films 21a and 22a facing each other is a distance at which plasma is not discharged in the portions except for the opening end portions 21x and 22x forming the fluid circulation holes 21b and 22b and the opening end portion 21y forming the through hole 21c, plasma is not generated in the portions except for the opening end portions.

[Effect of First Embodiment]

In accordance with the plasma generating apparatus 100 having such a configuration according to the embodiment, since plasma is generated only in the opening end portions forming the fluid circulation holes between the pair of electrodes 21 and 22, ions or radicals may be superiorly generated by generating plasma in the opening end portions and plasma is not generated in the portions except for the opening end portions in which ozone is superiorly generated. Consequently, it may be possible to sufficiently perform a function which deodorizes floating bacteria and adhesive bacteria by ions or radicals and a function which sterilizes the floating bacteria and adhesive bacteria by release of the ions or radicals to the outside of the apparatus, by increasing a generation amount of ions or radicals while suppressing generation of ozone. In addition, since at least a portion of the outlines of the respective corresponding fluid circulation holes 21b and 22b is configured so as to be arranged at positions different from each other, it may be possible to significantly increase a contact area between plasma and fluid passing through the fluid circulation holes 21b and 22b. Thus, it may be possible to increase a generation amount of ions or radicals.

[2. Second Embodiment]

Hereinafter, the second embodiment of the present invention will be described.

Figure 11:
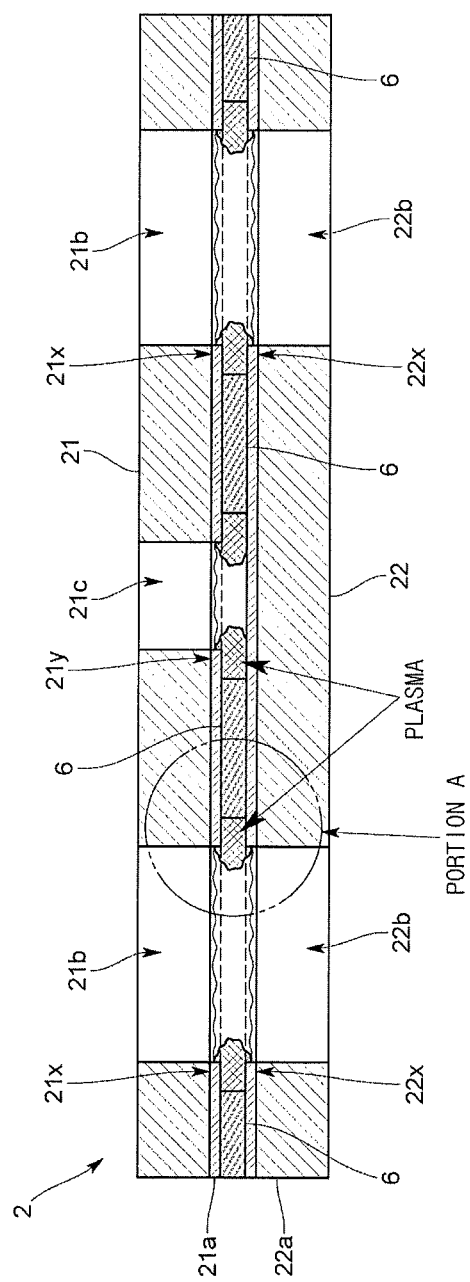
FIG. 11 is a partial enlarged cross-sectional view schematically illustrating a fluid circulation hole and a through hole according to a second embodiment.
Figure 12:
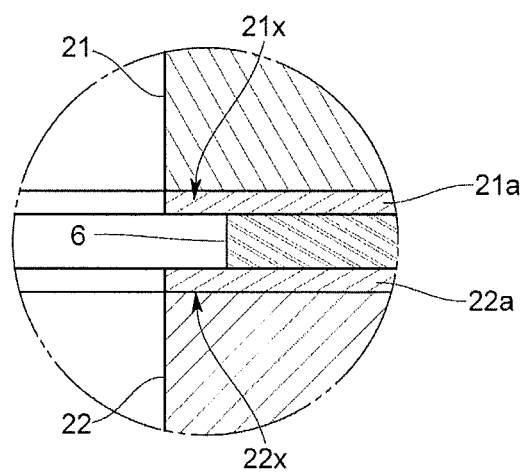
FIG. 12 is an enlarged cross-sectional view schematically illustrating an opening end portion forming the fluid circulation hole according to the second embodiment.

As shown in FIGS. 11 and 12, a plasma generating apparatus 100 according to the present embodiment includes plasma generation prevention members 6 which are provided to prevent generation of plasma in portions except for opening end portions 21x and 22x forming fluid circulation holes 21b and 22b and an opening end portion 21y forming a through hole 21c in a pair of electrodes 21 and 22.

Figure 13:
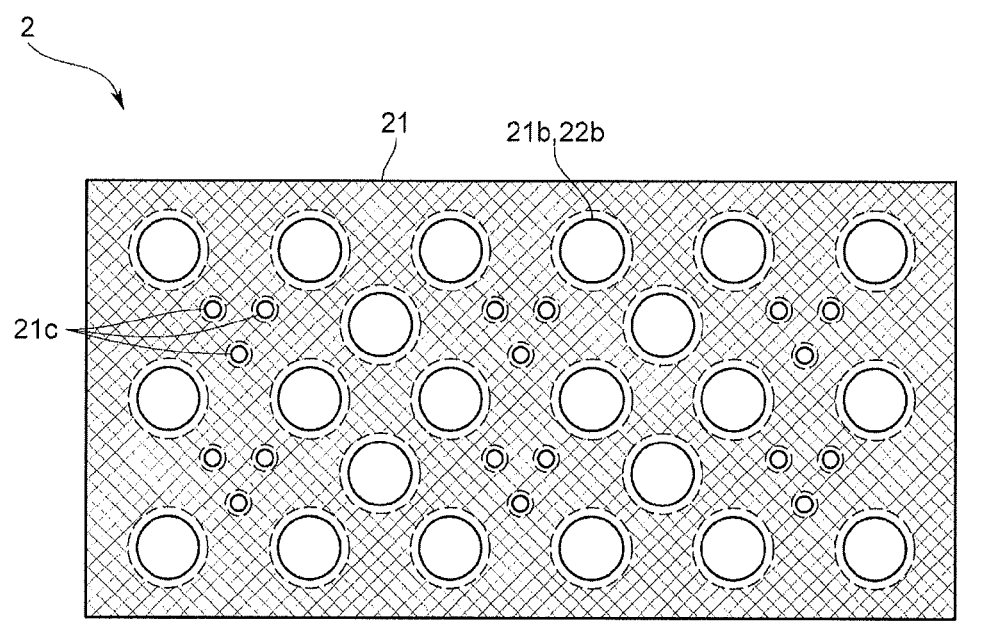
FIG. 13 is a top view schematically illustrating a position provided with a plasma generation prevention member according to the second embodiment.
Figure 13:

As shown in FIG. 13, the plasma generation prevention members 6 are provided beyond a range of 0 µm to 500 µm from opening ends forming the fluid circulation holes 21b and 22b and an opening end forming the through hole 21c between the pair of electrodes 21 and 22. In other words, the opening end portions 21x, 21y, and 22x are regions of 0 µm to 500 µm from the opening ends forming the fluid circulation holes 21b and 22b and the opening end forming the through hole 21c. In these regions, ozone is inferiorly generated compared to ions or radicals. In addition, in the embodiment, the plasma generation prevention members 6 are provided in the overall portion except for the opening end portions 21x, 21y, and 22x between the pair of electrodes 21 and 22. That is, the overall portion except for the opening end portions 21x, 21y, and 22x between the pair of electrodes 21 and 22 is filled with the plasma generation prevention members 6. Thus, plasma is not generated in the portions except for the opening end portions 21x, 21y, and 22x.

Each of the plasma generation prevention members 6 is most preferably made of a low dielectric material having a relative dielectric constant of 10 or less, and is made of a dielectric material having at least a relative dielectric constant of 30 or less. The low dielectric material includes, for example, alumina resin, urethane, ABS resin, natural rubber, nylon, ethylene resin, polyvinyl chloride resin, urea resin, butyl rubber, silicon rubber, quartz, and the like. The low dielectric material is provided to be pressed against the dielectric film 21a or 22a provided on the facing surface of each electrode 21 or 22 without general generation of a clearance therebetween. In this case, the pair of electrodes 21 and 22 may adhere to each other by the plasma generation prevention member 6 made of a low dielectric material having adhesion or a low dielectric material having adhesion by mixing an adhesive ingredient with a relative dielectric material. For example, low dielectric material includes epoxy resin, phenol resin, fluorine resin, polyester resin, silicon, vinyl acetate resin, methacrylic resin, and the like. Consequently, it may not be necessary to provide a separate fixing member for fixing the pair of electrodes 21 and 22 in a state of facing each other.

In addition, in a case where the plasma generation prevention member 6 is made of a low dielectric material which does not have adhesion, the plasma generation prevention member 6 may be interposed and fixed between the pair of electrodes 21 and 22. Besides, a method of providing the plasma generation prevention member 6 in the pair of electrodes 21 and 22 includes applying a low dielectric material on the dielectric films 21a and 22a of the respective electrodes 21 and 22 separated from each other and then overlapping the pair of electrodes 21 and 22 such that the dielectric films 21a and 22a face each other.

[Effect of Second Embodiment]

In accordance with the plasma generating apparatus 100 having such a configuration according to the embodiment, since the plasma generation prevention members 6 are provided in the portions except for the opening end portions 21x, 21y, and 22x forming the fluid circulation holes 21b and 22b and the through hole 21c, it may be possible to generate plasma in the opening end portions 21x, 21y, and 22x and to reduce plasma generated in the portions except for the opening end portions 21x, 21y, and 22x. Consequently, it may be possible to sufficiently perform a function which deodorizes floating bacteria and adhesive bacteria by ions or radicals and a function which sterilizes the floating bacteria and adhesive bacteria by release of the ions or radicals to the outside of the apparatus, by increasing a generation amount of ions or radicals while suppressing generation of ozone.

[3. Third Embodiment]

Hereinafter, the third embodiment of the present invention will be described.

Figure 14:
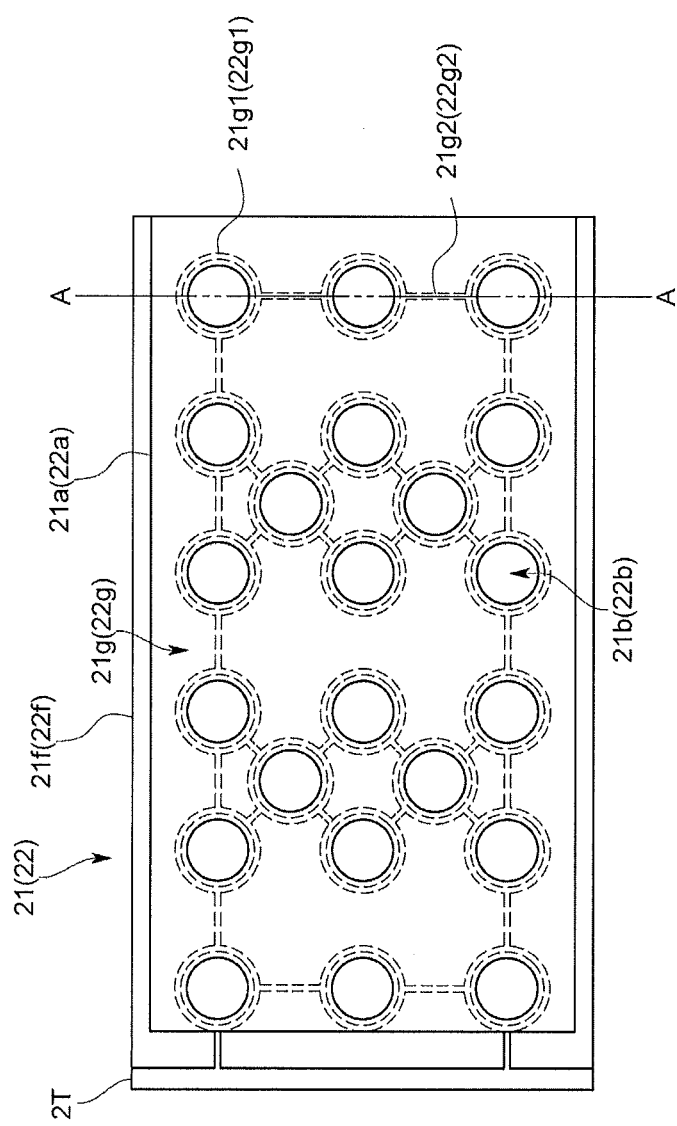
FIG. 14 is a top view illustrating an electrode according to a third embodiment when viewed from a facing surface side.
Figure 15:
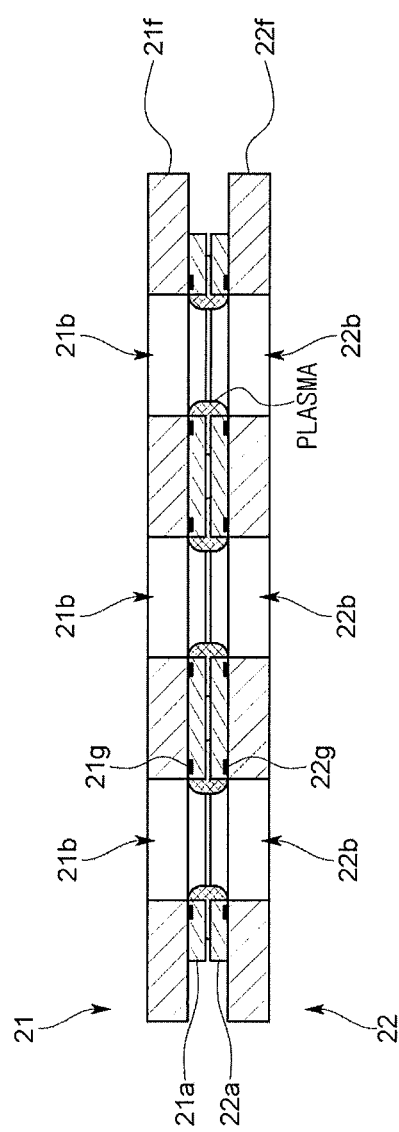
FIG. 15 is a cross-sectional view taken along line "A-A" of a plasma electrode portion according to the third embodiment.

As shown in FIGS. 14 and 15, a plasma generating apparatus 100 according to the present embodiment includes a pair of electrodes 21 and 22 in which conductive films 21g and 22g are provided in a region of discharging plasma of facing surfaces of ceramic substrates 21f and 22f and dielectric films 21a and 22a are provided on the conductive films 21g and 22g.

An edge portion of each electrode 21 or 22 is formed with an applied portions 2T to which a voltage is applied. Fluid circulation holes 21b and 22b are provided at positions corresponding to the respective electrodes 21 and 22 such that the respective electrodes 21 and 22 are configured to be penetrated as a whole by communication of the fluid circulation holes 21b and 22b.

The ceramic substrates 21f and 22f are made using a material such as CaO, $Al_2O_3$, $SiO_2$, $B_2O_3$, $ZrO_2$, $TiO_2$, or the like. The ceramic substrates 21f and 22f made of such a material may be formed by a method such as green sheet or press forming.

The conductive films 21g and 22g are formed on the facing surfaces of the ceramic substrates 21f and 22f by a method such as screen printing, gravure printing, inkjet, dispenser, or physical vapor deposition using a material containing Ag, Au, Cu, Ni, Pt, Pd, Ru, Ir, or the like as a constituent element thereof. Among others, it is preferable to a predetermined conductive pattern by forming a conductive paste including the various elements and applying the conductive paste on the ceramic substrates 21f and 22f by the method such as screen printing, gravure printing, inkjet, or dispenser.

The conductive films 21g and 22g are formed of annular conductive films 21g1 and 22g1 provided in opening end portion 21x and 22x of the fluid circulation holes 21b and 22b and linear conductive films 21g2 and 22g2 coming into electrical contact with the annular conductive films 21g1 and 22g1, which form a network. Each of the annular conductive films 21g1 and 22g1 is formed in a region within 1 mm, preferably in a region within 0.5 mm from an opening circumference of the associated fluid circulation hole 21b or 22b. Each of the linear conductive films 21g2 and 22g2 preferably has a width of 0.5 mm or less.

For example, the dielectric films 21a and 22a may be made of a material containing Ba, Ti, Ca, Zr, Sr, Y, Mg, or the like as a constituent element thereof.

Such a material may include, for example, an oxide, a carbide, a nitride, a boride, or the like. Specifically, the material may be, for example, BaO, $TiO_2$, CaO, ZrO, $Sr_2O_3$, $Y_2O_3$, MgO, $BaTiO_3$, $SrTiO_3$, BCTZ (barium calcium zirconate titanate (mixture of BaO, $TiO_2$, CaO, and ZrO)), BTZ (barium zirconate titanate (mixture of BaO, $TiO_2$, and ZrO)), $Zr_3B_4$, $SrB_6$, $CaB_6$, $MgB_2$, BN, TiN, ZrN, $Ca_3N_2$, $Si_3N_4$, SiC, TiC, $CaC_2$, ZrC, or the like. The dielectric films 21a and 22a are formed, for example, by a method such as green sheet, screen printing, gravure printing, inkjet, dispenser, or physical vapor deposition. The dielectric films 21a and 22a formed by the method are difficult to be porous.

The dielectric films 21a and 22a may have a surface roughness (calculated mean roughness Ra) of 5 to 50 μm. When the surface roughness of the dielectric films 21a and 22a is within the above range, a gap is defined between the facing surfaces only by overlapping the respective electrodes 21 and 22, so that plasma may be generated within the gap. Thus, a spacer to define a gap for plasma formation between the respective electrodes 21 and 22 is not required.

Such electrodes 21 and 22 may be manufactured by the following process, for example. The electrodes 21 and 22 are formed by (1) first, applying a conductive paste on the ceramic substrates 21f and 22f to form a predetermined conductive pattern, (2) next, overlapping materials of the dielectric films 21a and 22a on the conductive pattern, and (3) simultaneously heating and firing the ceramic substrates 21f and 22f, the conductive pattern, and the materials of the dielectric films 21a and 22a.

Specifically, the electrode manufacturing method includes, for example, (A) an LTCC (Low Temperature Co-Fired Ceramic) method or (B) a press substrate/printing method.

(A) The LTCC method manufactures an electrode by the following procedures.

(1) Slurry for a green sheet for a ceramic substrate is manufacture by properly mixing binder, sintering agent, plasticizer, dispersing agent, organic solvent, or the like with ceramic powder.

(2) A green sheet for a ceramic substrate is manufacture by forming the obtained slurry in a predetermined thickness by a doctor blade method or a printing method and drying the same.

(3) A conductive pattern is formed by forming a conductive paste on the obtained green sheet for a ceramic substrate in a predetermined pattern by screen printing and is then dried. In addition, the conductive paste may also use a commercial paste (for example, DD-1141A manufactured by Kyoto electronic cooking company).

(4) Surry for a green sheet for a dielectric film is manufacture by properly mixing binder, sintering agent, plasticizer, dispersing agent, organic solvent, or the like with ceramic powder.

(5) A green sheet for a dielectric film is manufacture by forming the obtained slurry in a predetermined thickness or shape by a doctor blade method or a printing method.

(6) The green sheet for a dielectric film obtained by (5) is laminated on and pressed against the green sheet for a ceramic substrate formed with the conductive pattern obtained by (3) by a press or a calendar roll.

(7) The obtained laminated body is formed with a hole at a predetermined position thereof, is cut in an element size, and is then fired at high temperature.

(B) The press substrate/printing method manufactures an electrode by the following procedures.

(1) A ceramic substrate 21f or 22f is manufacture by inserting ceramic powder into a mold having a predetermined size and pressing the same.

(2) The obtained ceramic substrate 21f or 22f is formed with a hole at a predetermined position thereof, and is then cut in an element size by laser or a press.

(3) A conductive pattern is formed by forming a conductive paste on the cut ceramic substrate 21f or 22f in a predetermined pattern by screen printing and is then dried.

(4) A dielectric paste is manufactured by mixing binder and dielectric powder, dispersing the same by three rolls, and then diluting the same with solvent so as to have viscosity easy to print.

(5) A dielectric film 21a or 22a is formed by printing the dielectric paste obtained by (4) on a predetermined position of the ceramic substrate 21f or 22f formed with the conductive pattern obtained by (3) and is then fired at high temperature.

The plasma generating apparatus 100 according to the present embodiment performs deodorization in the vicinity of the electrodes 21 and 22 by generating plasma in a region formed with the conductive films 21g and 22g of gaps between two facing electrodes 21 and 22 and sending wind to the fluid circulation holes 21b and 22b using the blower mechanism 3, and performs sterilization of adhesive bacteria by releasing active species generated during plasma to a closed space.

[Effect of Third Embodiment]

In accordance with the plasma generating apparatus 100 having such a configuration according to the embodiment, it may be possible to superiorly generate active species such as ions or radicals and reduce a generation amount of ozone by selectively performing plasma discharge in the opening end portions 21x and 22x of the fluid circulation holes 21b and 22b.

In addition, since the ceramic substrates 21f and 22f for the electrodes are manufactured from ceramic powder in the plasma generating apparatus 100 according to the embodiment, it may be possible to form the electrodes in various shapes and obtain the degree of freedom of design with respect to the electrodes according to use thereof.

Furthermore, since the electrodes 21 and 22 are manufactured by one firing process in the plasma generating apparatus 100 according to the embodiment, it may be possible to manufacture the electrodes by an easy method compared to the related art and by a minimal process and to reduce manufacturing costs.

[Other Modified Embodiments]

The present invention is not limited to the above-mentioned embodiments.

Figure 16:
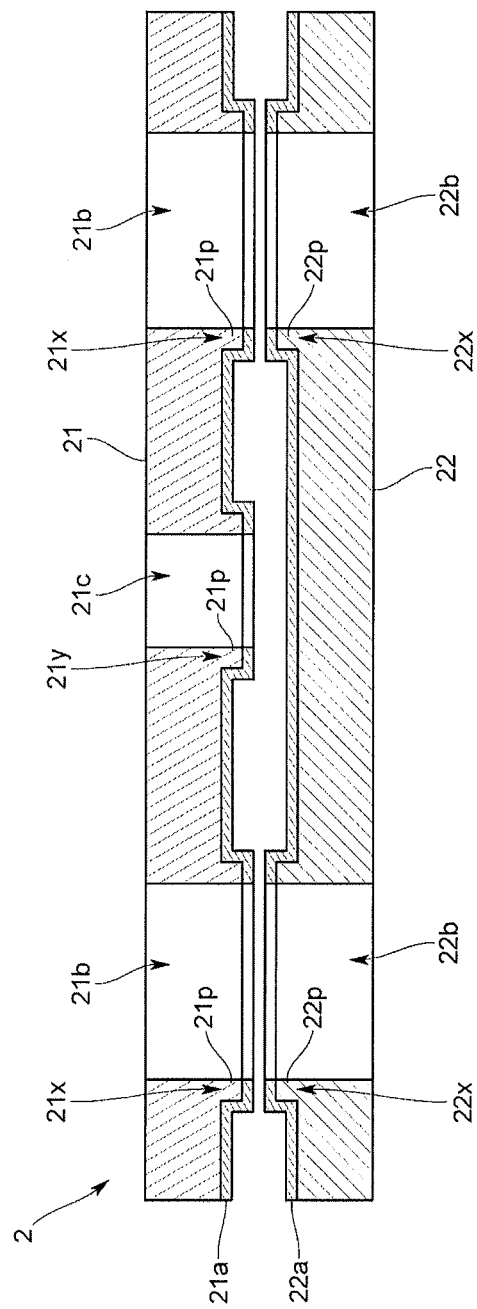
FIG. 16 is a partial enlarged cross-sectional view schematically illustrating a fluid circulation hole and a through hole according to a modified embodiment.

For example, although plasma is generated only in the opening end portions by controlling the thicknesses of the dielectric films 21a and 22b in the first embodiment, annular protrusion portions 21p and 220 may also be provided integrally in the opening end portions 21x, 21y, and 22x on the facing surfaces of the electrodes 21 and 22 as shown in FIG. 16. In this case, by arranging the dielectric films 21a and 22b on the facing surfaces of the electrodes 21 and 22, a facing distance L1 between the opening end portions 21x and 22x forming the fluid circulation holes 21b and 22b facing each other and a facing distance L2 between the opening end portion 21y forming the through hole 21c and the dielectric film 22a facing the same may be configured to be smaller than a facing distance L3 between portions except for the opening end portions.

Figure 17:
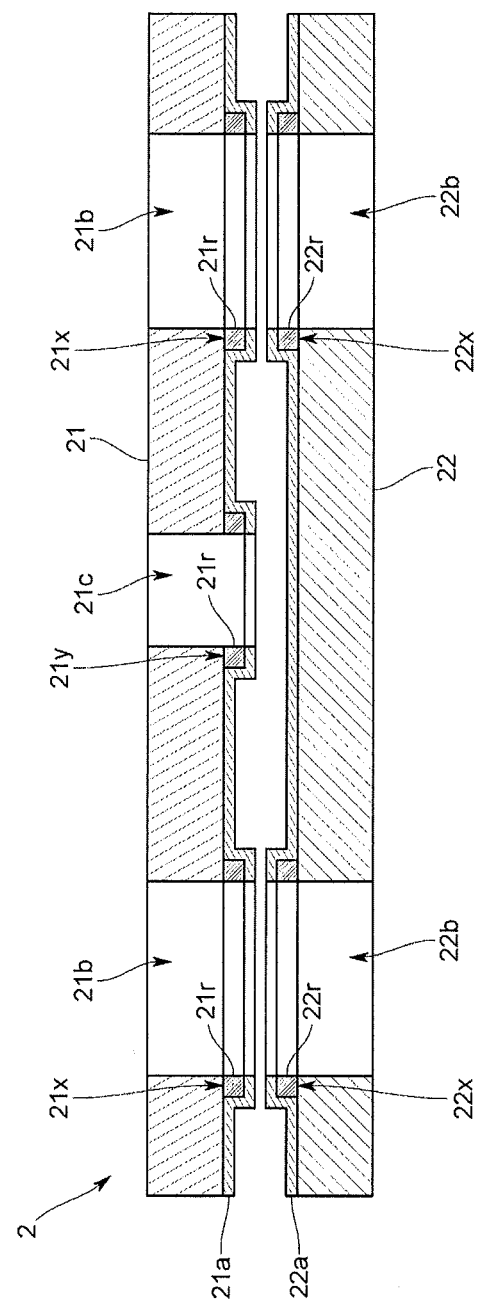
FIG. 17 is a partial enlarged cross-sectional view schematically illustrating a fluid circulation hole and a through hole according to a modified embodiment.

In addition, as shown in FIG. 17, annular ring members 21r and 22r may also be provided in the opening end portions 21x, 21y, and 22x on the facing surfaces of the electrodes 21 and 22 so that the dielectric films 21a and 22b are provided on the facing surfaces of the electrodes 21 and 22. Consequently, it may be possible to reduce process costs compared to integrally providing the protrusion portion by cutting the electrode.

Figure 18:
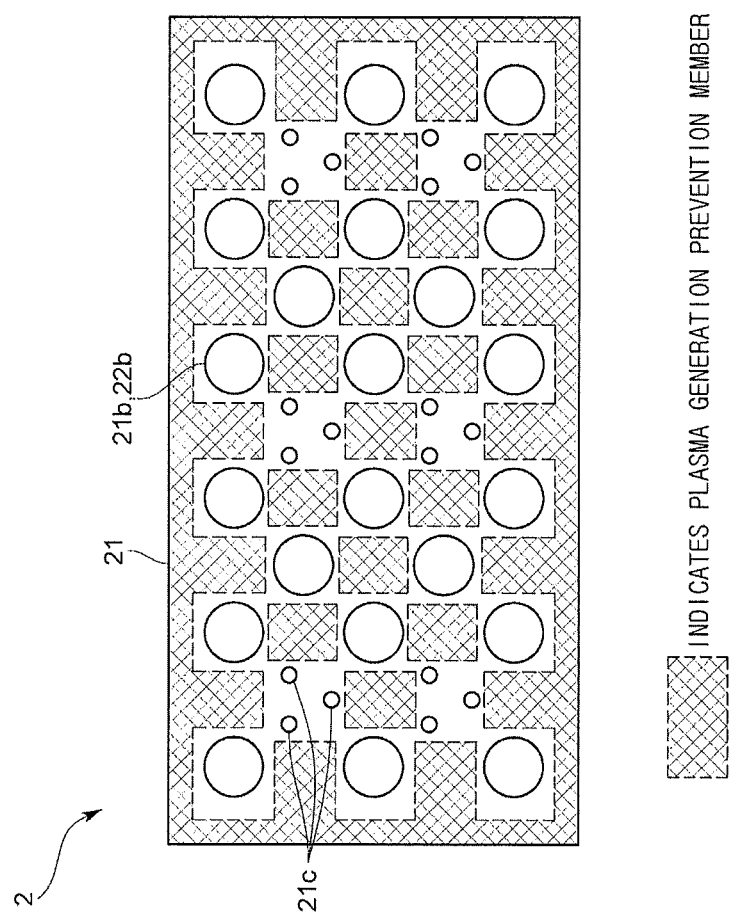
FIG. 18 is a top view schematically illustrating a position provided with a plasma generation prevention member according to a modified embodiment.

In addition, although the plasma generation prevention members 6 are provided in the overall portion except for the opening end portions in the above embodiment, the plasma generation prevention members 6 may also be partially provided in the portions except for the opening end portions as shown in FIG. 18. Consequently, it may be possible to reduce plasma generated in the portions except for the opening end portions and thus reduce a generation amount of ozone.

Figure 19:
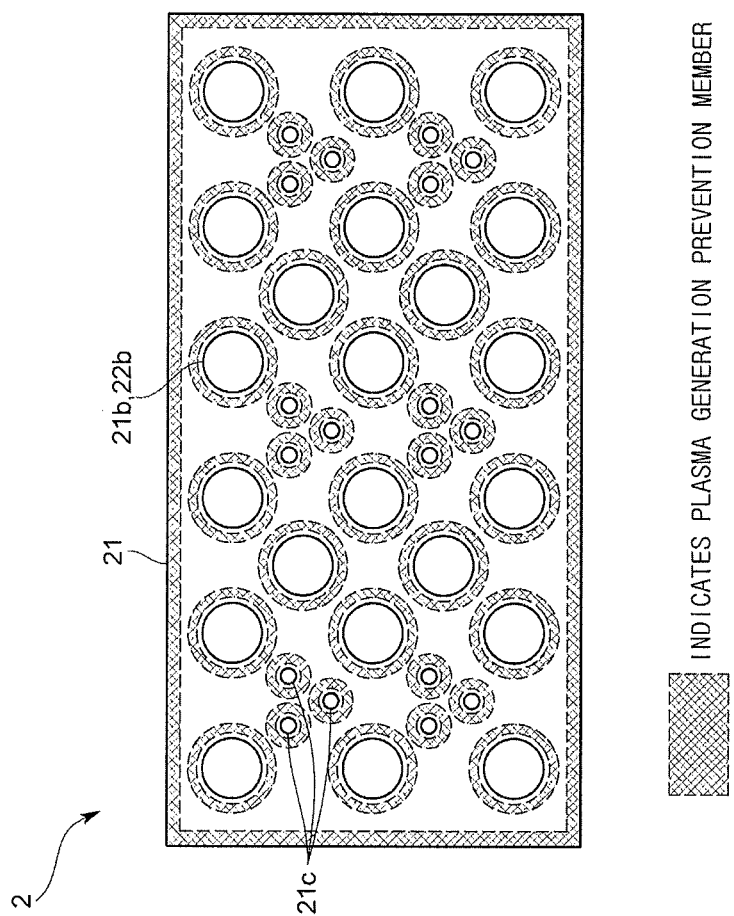
FIG. 19 is a top view schematically illustrating a position provided with a plasma generation prevention member according to a modified embodiment.

In addition, as shown in FIG. 19, the plasma generation prevention members 6 may also be formed in an annular shape so as to cover the circumferences of the opening end portions 21x and 22x of the fluid circulation holes 21b and 22b and the opening end portion 21y of the through hole 21c. In this case, the annular plasma generation prevention members 6 formed to cover the circumferences of the opening end portions 21x, 21y, and 22x also have a function of preventing ozone generated within the electrodes from being released from the fluid circulation holes 21b and 22b and the through hole 21c to the outside. Consequently, it may be possible to reduce an amount of low dielectric material used to make the plasma generation prevention members 6 and to reduce material costs.

Figure 20:
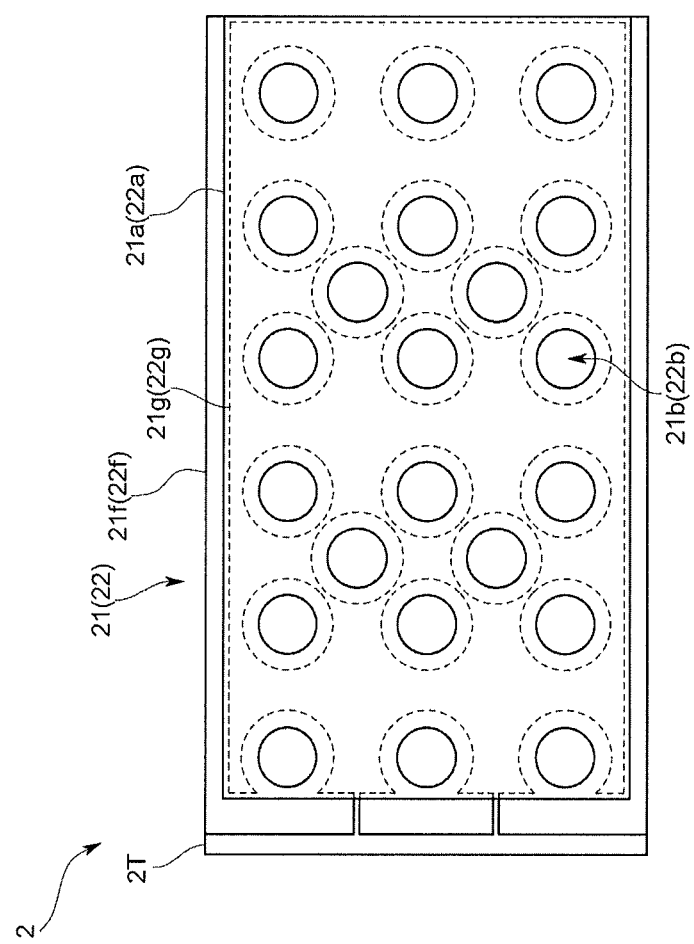
FIG. 20 is a top view illustrating an electrode according to a modified embodiment when viewed from a facing surface side.

As shown in FIG. 20, each conductive film 21g or 22g may also be formed in a planar shape in a region spaced over 1 mm from an opening circumference of the associated fluid circulation hole 21b or 22b. Consequently, it may be possible to superiorly generate long-lived ozone compared to active species such as ions or radicals. Accordingly, the plasma generating apparatus 100 according to the embodiment is proper for a case of high odor concentrations, a case where floating bacteria or adhesive bacteria having high concentrations are present, or a case of being used in a space in which the human or pet is not locally present.

Figure 21:
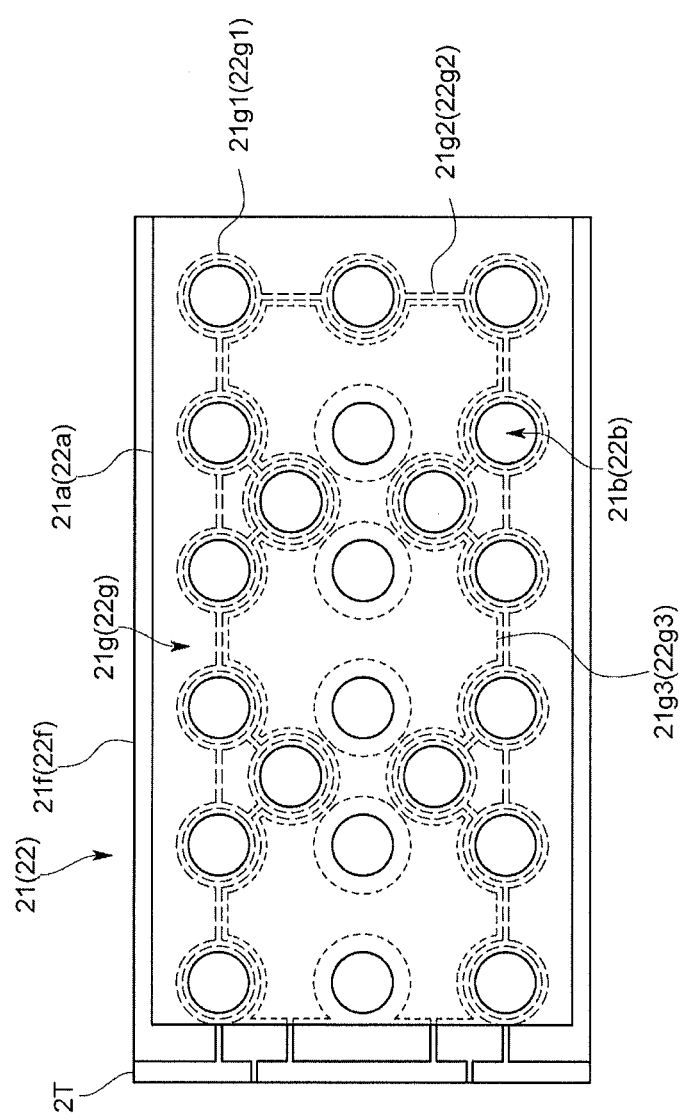
FIG. 21 is a top view illustrating an electrode according to a modified embodiment when viewed from a facing surface side.
Figure 22:
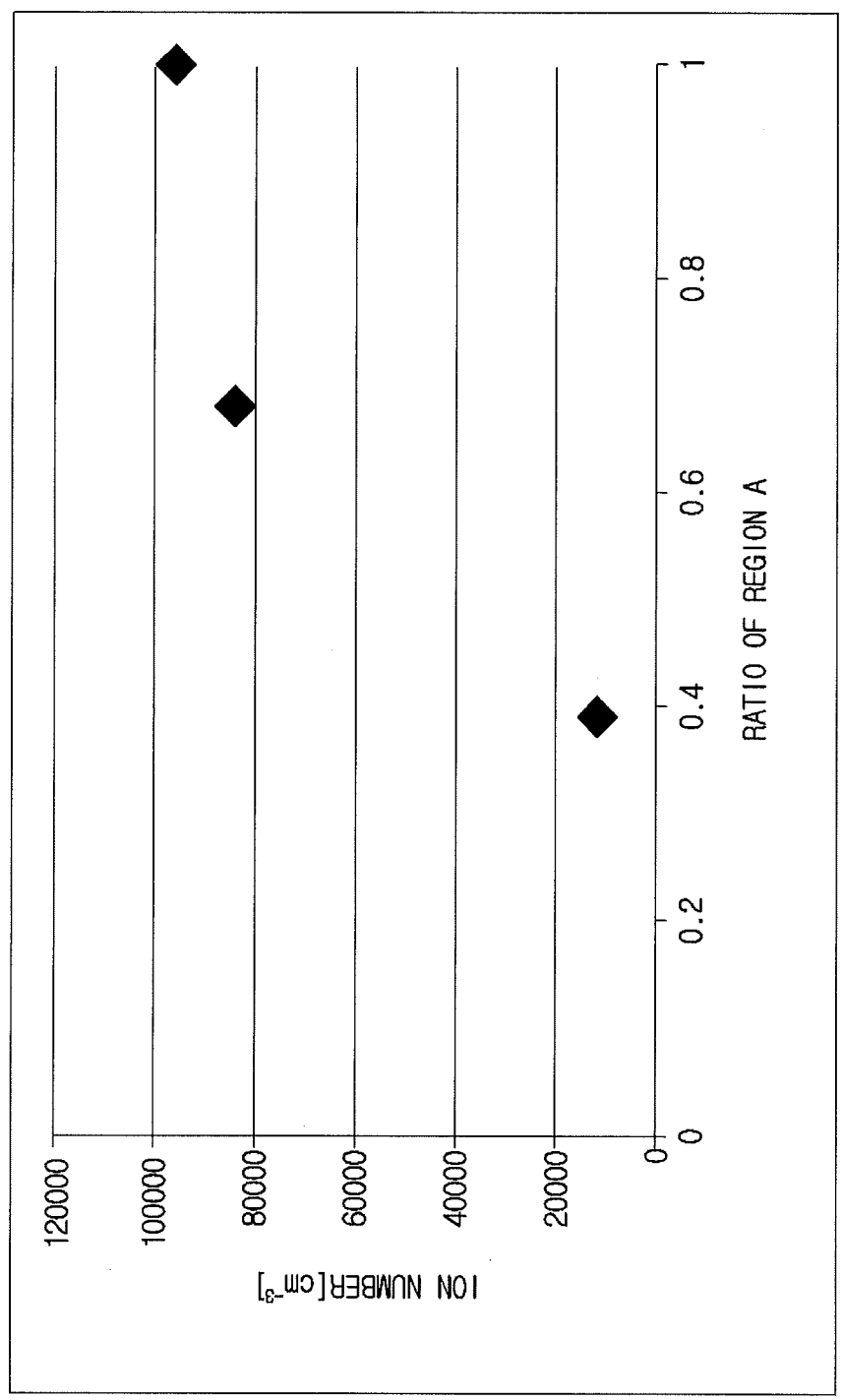
FIG. 22 is a graph illustrating an ion number when plasma is discharged into three types of electrodes having through holes which are differently arranged from each other.
Figure 23:
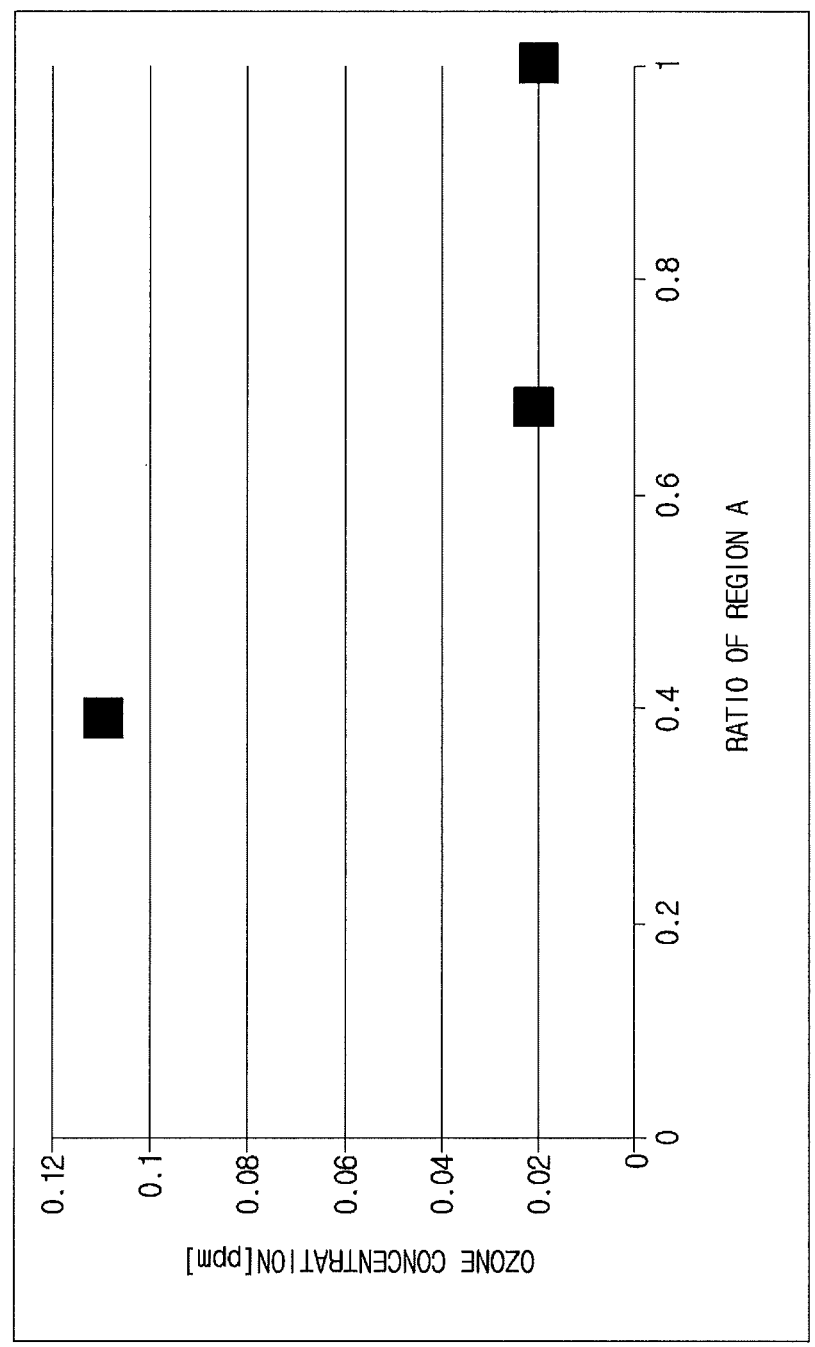
FIG. 23 is a graph illustrating an ozone concentration when plasma is discharged into three types of electrodes having through holes which are differently arranged from each other.

In addition, as shown in FIG. 21, the conductive films 21g and 22g may also be configured by annular conductive films 21g1 and 22g1 formed in the opening end portion 21x and 22x of the fluid circulation holes 21b and 22b, linear conductive films 21g2 and 22g2 coming into contact with the annular conductive films 21g1 and 22g1, and planar conductive films 21g3 and 22g3 formed in a planar shape in regions except for opening peripheral portions of the fluid circulation holes 21b and 22b. In addition, a network configured by the annular conductive films 21g1 and 22g1 and the linear conductive films 21g2 and 22g2 is electrically isolated from the planar conductive films 21g3 and 22g3. Consequently, by controlling what to apply a voltage to any one of the network configured by the annular conductive films 21g1 and 22g1 and the linear conductive films 21g2 and 22g2 and the planar conductive films 21g3 and 22g3, it may be possible to properly select what to superiorly generate any one of active species such as ions or radicals and the ozone and to control the same. Accordingly, in a case of low odor concentrations, a case where floating bacteria or adhesive bacteria having low concentrations are present, or a case of being used in a space in which the human or pet is locally present, it may be possible to superiorly generate active species such as ions or radicals by applying a voltage to the network configured by the annular conductive films 21g1 and 22g1 and the linear conductive films 21g2 and 22g2. On the other hand, in a case of high odor concentrations, a case where floating bacteria or adhesive bacteria having high concentrations are present, or a case of being used in a space in which the human or pet is not locally present, it may be possible to superiorly generate ozone.

The dielectric films 21a and 22a may not be formed on the entirety of the facing surfaces of the ceramic substrates 21f and 22f and may also be formed only on the conductive films 21g and 22g. It may be possible to accurately control generation regions of active species such as ions or radicals and ozone by limiting the formation regions of the dielectric films 21a and 22a to only the conductive films 21g and 22g. In particular, this is effective to superiorly generate active species such as ions or radicals while suppressing generation of ozone. In addition, it may be possible to reduce manufacturing costs by limiting the formation regions of the dielectric films 21a and 22a.

In addition, although the thickness of the dielectric film throughout circumference of the opening end portion is thicker than the thickness of the dielectric film at a portion except for the same in the above embodiment, the thickness of the dielectric film at a portion of the opening end portion may also be thicker than the thickness of the dielectric film at a portion except for the same.

For example, although the coating film is provided on the dielectric films of the respective electrodes in the above embodiment, the same effect may be realized even when the coating film is provided on any one of the dielectric films.

In addition, although the plural fluid circulation holes 21b of the electrode 21 have the same shape and the plural fluid circulation holes 22b of the electrode 22 have the same shape in the above embodiment, these may also be formed in different shapes.

Furthermore, although the through hole is formed at either the electrode 21 of one side or the electrode 22 of the other side in the above embodiment, the through hole (half opening portion) may also be formed at both thereof.

Moreover, although the fluid circulation holes have the same cross-section shape in the above embodiment, the fluid circulation hole formed in each electrode may also have a tapered surface, a conical shape or bowl shape. That is, the fluid circulation hole may have a reduced diameter or an enlarged diameter as being advanced from one opening to the other opening.

In addition, the fluid circulation hole may also have a circular shape, an elliptical shape, a rectangular shape, a linear slit shape, a concentric circular slit shape, a waveform slit shape, a lunular shape, a comb shape, a honeycomb shape, or a star shape.

In addition, the present invention is not limited to the above embodiment, and various modifications are possible without departing from the scope and spirit of the invention.

Various embodiments have been described in the best mode for carrying out the invention.

INDUSTRIAL APPLICABILITY

In accordance with a plasma generating apparatus according to the present invention, it may be possible to sufficiently perform a function which deodorizes floating bacteria and adhesive bacteria by ions or radicals and a function which sterilizes the floating bacteria and adhesive bacteria by release of the ions or radicals to the outside of the apparatus, by increasing a generation amount of ions or radicals while suppressing generation of ozone.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A plasma generating apparatus comprising:
at least one pair of electrodes including a first electrode facing a second electrode;
a first dielectric film on at least part of a surface of the first electrode facing the second electrode, a second dielectric film on at least part a surface of the second electrode facing the first electrode with a gap between the first dielectric film and the second dielectric film, and configured to apply a predetermined voltage between the first electrode and the second electrode to discharge plasma,
wherein fluid circulation holes are respectively provided at corresponding positions of the respective at least one pair of electrodes and pass through the at least one pair of electrodes and plasma is generated only in opening end portions forming the fluid circulation holes between the at least one pair of electrodes.

2. The plasma generating apparatus according to claim 1, wherein:
a facing distance between the opening end portions forming the fluid circulation holes is smaller than a facing distance between portions except for the opening end portions; and
if the predetermined voltage is applied between the at least one pair of electrodes, plasma is discharged only in the opening end portions forming the fluid circulation holes.

3. The plasma generating apparatus according to claim 2, wherein a thickness of the dielectric film at each of the opening end portions forming the fluid circulation holes is thicker than a thickness of the dielectric film at the portion except for the opening end portions.

4. The plasma generating apparatus according to claim 3, wherein a thickness of the dielectric film formed on an overall circumference of each of the opening end portions is thicker than a thickness of the dielectric film at the portion except for the opening end portions.

5. The plasma generating apparatus according to claim 3, wherein a difference between the thickness of the dielectric film at each of the opening end portions and the thickness of the dielectric film at the portion except for the opening end portions is 1 µm to 500 µm.

6. The plasma generating apparatus according to claim 1, wherein a plasma generation prevention member to prevent generation of plasma is provided in a portion except for the opening end portions forming the fluid circulation holes of the respective at least one pair of electrodes.

7. The plasma generating apparatus according to claim 6, wherein the plasma generation prevention member is provided beyond a range of 0 µm to 500 µm from an opening end forming each of the fluid circulation holes.

8. The plasma generating apparatus according to claim 6, wherein the plasma generation prevention member is provided in an overall portion except for the opening end portions between the at least one pair of electrodes.

9. The plasma generating apparatus according to claim 6, wherein the plasma generation prevention member is made of a low dielectric material having a relative dielectric constant of 30 or less.

10. The plasma generating apparatus according to claim 6, wherein the plasma generation prevention member is pressed against the facing surface of each the first electrode and the second electrode or the dielectric film.

11. The plasma generating apparatus according to claim 6, wherein the at least one pair of electrodes adhere to each other by the plasma generation prevention member.

12. The plasma generating apparatus according to claim 6, wherein the plasma generation prevention member is interposed and fixed between the at least one pair of electrodes.

13. The plasma generating apparatus according to claim 1, wherein each of the opening end portions forming the fluid circulation holes on the facing surfaces is formed with an annular protrusion portion, and the dielectric film is provided on the facing surface formed with the annular protrusion portion.

14. The plasma generating apparatus according to claim 1, wherein the dielectric film is formed only in each of the opening end portions forming the fluid circulation holes on the facing surfaces.

15. The plasma generating apparatus according to claim 1, wherein a blower mechanism is provided upstream or downstream of the fluid circulation holes and wind is blown into the fluid circulation holes by the blower mechanism.

16. The plasma generating apparatus according to claim 1, wherein the dielectric film is formed by sputtering.

17. The plasma generating apparatus according to claim 1, wherein the voltage applied to each of the first electrode and the second electrode is formed in a pulse shape, a peak value thereof is set within a range of 100 V to 5000 V, and a pulse width is set within a range of 0.1 µs to 300 µs.

* * * * *